US005663292A

United States Patent [19]
Rivier

[11] Patent Number: 5,663,292
[45] Date of Patent: Sep. 2, 1997

[54] CYCLIC CRF ANALOGS

[75] Inventor: Jean E. F. Rivier, La Jolla, Calif.

[73] Assignee: The Salk Institute for Biological Studies, San Diego, Calif.

[21] Appl. No.: 353,928

[22] Filed: Dec. 12, 1994

[51] Int. Cl.$^6$ .............................. C07K 14/695; C07K 7/64
[52] U.S. Cl. .............................. 530/306; 530/317; 930/21; 930/70; 930/260
[58] Field of Search ...................... 530/306, 317; 514/9, 2, 805; 930/21, 70, 260

[56] References Cited

U.S. PATENT DOCUMENTS

| | | | |
|---|---|---|---|
| 4,632,780 | 12/1986 | Seidah et al. | 560/306 |
| 5,064,939 | 11/1991 | Rivier et al. | 530/317 |
| 5,109,111 | 4/1992 | Rivier et al. | 530/306 |
| 5,245,009 | 9/1993 | Kornreich et al. | 530/306 |
| 5,278,146 | 1/1994 | Rivier et al. | 514/12 |

OTHER PUBLICATIONS

Life Sciences, vol. 51, pp. 189–193, 1992 (Hniby).
Biopolymers, vol. 31, pp. 745–750, 1991 (Gilon).

*Primary Examiner*—Christina Y. Chan
*Assistant Examiner*—J. D. Wessendorf
*Attorney, Agent, or Firm*—Fitch, Even, Tabin & Flannery

[57] ABSTRACT

Improved CRF antagonist peptides have the formula:

(cyclo 30–33)D—Phe—His—Leu—Leu—Arg—Glu—Val—

—Leu—Glu—Nle—Ala—Arg—Ala—Glu—Gln—Leu—

—Ala—Gln—$R_{30}$—Ala—His—$R_{33}$—Asn—Arg—Lys—

—Leu—Nle—Glu—Ile—Ile—$NH_2$ wherein $R_{30}$ is Cys or Glu; $R_{33}$ is Cys, Lys or Orn; provided that when $R_{30}$ is Cys, $R_{33}$ is Cys and when $R_{30}$ is Glu, $R_{33}$ is Lys or Orn. The N-terminus may be extended by Asp-Leu-Thr. Lys may be substituted for $Arg^{23}$ and its side chain connected by a lactam bridge to $Glu^{20}$ to form a dicyclic peptide. Specific CRF antagonists disclosed include (cyclo 30-33) [D-Phe$^{12}$, Nle$^{21,38}$, Glu$^{30}$, Lys$^{33}$]rCRF(12-41); (cyclo 30-33) [D-Phe$^{12}$, Nle$^{21,38}$, Glu$^{30}$, Orn$^{33}$]rCRF(12-41), (cyclo 30-33) [D-Phe$^{12}$, Nle$^{21,38}$, Cys$^{30,33}$]rCRF (12-41) and (bicyclo 20-23,30-33) [D-Phe$^{12}$, Nle$^{21,38}$, Lys$^{23,33}$, Glu$^{30}$]-rCRF(12-41).

16 Claims, No Drawings

CYCLIC CRF ANALOGS

This invention was made with Government support under grant number DK-26741 awarded by the National Institutes of Health. The Government has certain rights in this invention.

This invention is directed to peptides and to methods for pharmaceutical treatment of mammals using such peptides. More specifically, the invention relates to cyclic analogs of the hentetracontapeptide CRF, particularly antagonists thereof, to pharmaceutical compositions containing such cyclic CRF analogs and to methods of treatment of mammals using such cyclic CRF analogs.

BACKGROUND OF THE INVENTION

Experimental and clinical observations have supported the concept that the hypothalamus plays a key role in the regulation of adenohypophysial corticotropic cells' secretory functions. Over 25 years ago it was demonstrated that factors present in the hypothalamus would increase the rate of ACTH secretion by the pituitary gland when incubated in vitro or maintained in an organ culture. However, a physiologic corticotropin releasing factor (CRF) was not characterized until ovine CRF (oCRF) was characterized in 1981. As disclosed in U.S. Pat. No. 4,415,558, the disclosure of which is incorporated herein by reference, oCRF was found to be a 41-residue amidated peptide. oCRF lowers blood pressure in mammals when injected peripherally and stimulates the secretion of ACTH and β-endorphin.

Rat CRF (rCRF) was later isolated, purified and characterized; it was found to be a homologous, amidated hentetracontapeptide as described in U.S. Pat. No. 4,489,163, the disclosure of which is incorporated herein by reference. The formula of human CRF has now been determined to be the same as that of rCRF, and the terms rCRF and hCRF are used interchangeably.

A CRF analog was subsequently developed having a high alpha-helical forming potential which is also a 41-residue amidated peptide. It is commonly referred to as AHC (alpha-helical CRF) and is described in U.S. Pat. No. 4,594,329, the disclosure of which is incorporated herein by reference. Other analogs containing D-isomers were developed, such as those shown in U.S. Pat. No. 5,278,146.

Synthetic rCRF, oCRF and AHC stimulate ACTH and β-endorphin-like activities (β-END-Li) in vitro and in vivo and substantially lower blood pressure when injected peripherally. Antagonists of these compounds are disclosed in U.S. Pat. No. 4,605,642, issued Aug. 12, 1986, the disclosure of which is incorporated herein by reference. Cyclic CRF analogs exhibiting biopotency have been developed as disclosed in U.S. Pat. No. 5,245,009 (Sep. 14, 1993) and in pending U.S. patent application Ser. No. 78,558, filed Jun. 16, 1993, now U.S. Pat. No. 5,493,006.

Since the foregoing discoveries, the search for improved CRF analogs has continued.

SUMMARY OF THE INVENTION

Analogs of these CRF peptides have been discovered which exhibit longer lasting and improved biological activity. Certain analogs which are of particular interest are novel CRF antagonists that have improved biological properties in comparison to known CRF antagonists and may exhibit substantially no residual CRF agonist activity. These peptides have a cyclizing bond between the residues in the 30- and 33-positions and may optionally have a second such bond between the residues in the 20- and 23-positions. Either or both of these bonds may be a disulfide linkage between two Cys residues, but they are preferably each an amide bond (or lactam bridge) between side chain carboxyl and amino groups. Most preferably there is a lactam bridge between a side chain carboxyl group on the residue in the 30-position, preferably Glu, and a side chain amino group on the 33-position residue, preferably Lys or Orn. The most preferred option is a lactam bridge between Glu in the 20-position and Lys in the 23-position.

These peptides also have the preferred optional substitutions of D-Phe or an equivalent D-isomer in the 12-position and norleucine in the 21 and 38 positions. Other optional substitutions may also be made throughout the molecule as previously taught, and these are considered to be functional equivalents thereof. For example, the Leu residue in the 37-position can be substituted with a methyl group on its α-carbon atom, as can be other Leu residues throughout the molecule, and such substitutions, both alone and in combination with the aforementioned substitutions, are considered to enhance biopotency. The 41-residue peptide is shortened at the N-terminus to produce the CRF antagonists, preferably by deletion of a sequence of 8 to 11 residues. Advantages also flow from the employment of these substitutions in the entire 41-residue peptide or in equivalent versions shortened at the N-terminus by up to 3–5 residues, i.e. improved cyclic CRF agonists.

Pharmaceutical compositions in accordance with the invention include such CRF analogs, including the antagonists, or nontoxic addition salts thereof that are dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, β-endorphin, β-lipotropin, corticosterone and other products of the pro-opiomelanocortin gene and/or for affecting mood, behavioral and gastrointestinal functions and autonomic nervous system activities. For example, these CRF antagonists may be administered to reduce high ACTH levels, and thereby treat stress-related illnesses, such as stress-induced depression and anxiety, to raise blood pressure when injected iv, to decrease blood flow to the gastrointestinal tract, i.e. particularly to treat patients suffering from abdominal bowel syndrome and gastrointestinal diseases, and also to treat inflammatory diseases; immune suppression; human immunodeficiency virus (HIV) infections; Alzheimer's disease; anorexia nervosa; hemorrhagic stress; drug and alcohol withdrawal symptoms; drug addiction; and fertility problems.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Abu=L-2-aminobutyric acid, Dbu=L-2,4-diaminobutyric acid, Dpr=L-2,3-diaminopropionic acid, and Har=L-homoarginine. In addition the following abbreviations are used: CML= $C^\alpha CH_3$-L-leucine; Aib=$C^\alpha CH_3$-L-alanine or 2-aminoisobutyric acid; Nal=L-β-(1- or 2-naphthyl) alanine and Pal=L-β-(2-, 3- or 4-pyridyl) alanine.

Generally the CRF antagonists include a D-isomer in the 12-position (which may be the N-terminus) and have the formula, or are nontoxic salts thereof:

(cyclo 30-33)Y-$R_{12}$-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$Nle-$R_{39}$-$R_{40}$-$R_{41}$-$NH_2$ wherein Y is an acylating agent having up to 7 carbon atoms, e.g. Ac, Fr, Acr and Bz, or hydrogen; $R_{12}$ is D-Phe, D-Tyr, D-ClPhe, D-Nal or D-Pal; $R_{13}$ is His, Tyr or Glu; $R_{14}$ is CML or Leu; $R_{15}$ is CML or Leu; $R_{17}$ is Cys or CML, Glu, Asn or Lys; $R_{18}$ is Val, Nle or Met; $R_{19}$ is CML, Leu, Ile, Ala or Aib; $R_{20}$ is Glu, D-Glu, Cys or His; $R_{22}$ is Ala, Aib, Thr, Asp or Glu; $R_{23}$ is Arg, Cys, Orn or Lys; $R_{24}$ is Ala or Aib; $R_{25}$ is Asp or Glu; $R_{26}$ is Gln, Asn or Lys; $R_{27}$ is CML or Leu; $R_{28}$ is Ala or Aib; $R_{29}$ is Gln, Aib or Glu; $R_{30}$ is Glu or Cys; $R_{31}$ is Ala or Aib; $R_{32}$ is His, Aib, Gly, Tyr or Ala; $R_{33}$ is Lys, Orn or Cys; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; and wherein Thr, Leu-Thr or Asp-Leu-Thr can be optionally provided at the N-terminus; provided that when $R_{30}$ is Glu, $R_{33}$ is Lys or Orn and when $R_{30}$ is Cys, $R_{33}$ is Cys, and provided further that a second cyclizing bond may exist between $R_{20}$ and $R_{23}$. If a second cyclizing bond is present, preferably both bonds are not Cys-Cys.

A preferred group of antagonists are those having the formula or are nontoxic salts thereof:

(cyclo 30-33)D-Phe-His-Leu-Leu-Arg-Glu-$R_{18}$-Leu-$R_{20}$-Nle-$R_{22}$-$R_{23}$-Ala-$R_{25}$-Gln-Leu-Ala-$R_{29}$-$R_{30}$-Ala-$R_{32}$-$R_{33}$-$R_{34}$-Arg-$R_{36}$-Leu-Nle-$R_{39}$-$R_{40}$-$R_{41}$-$NH_2$ wherein $R_{18}$ is Val, Nle or Met; $R_{20}$ is Glu, D-Glu, Cys or His; $R_{22}$ is Ala or Thr; $R_{23}$ is Arg, Cys, Orn or Lys; $R_{25}$ is Asp or Glu; $R_{29}$ is Gln or Glu; $R_{30}$ is Glu or Cys; $R_{32}$ is His or Ala; $R_{33}$ is Lys, Cys or Orn; $R_{34}$ is Asn or Aib; $R_{36}$ is Lys or Leu; $R_{39}$ is Glu or Asp; $R_{40}$ is Ile or Glu; and $R_{41}$ is Ile or Ala; and wherein Thr, Leu-Thr or Asp-Leu-Thr can be optionally provided at the N-terminus; provided that when $R_{30}$ is Cys, $R_{33}$ is Cys; and when $R_{30}$ is Glu, $R_{33}$ is Orn or Lys; and provided further that a second cyclizing bond may exist between $R_{20}$ and $R_{23}$.

A more preferred group of CRF antagonists are those having the formula or are nontoxic salts thereof:

(cyclo 30-33)Y-D-Phe-His-Leu-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-His-$R_{33}$-$R_{34}$-Arg-Lys-Leu-Nle-$R_{39}$-Ile-$R_{41}$-$NH_2$ wherein Y is Ac or H; $R_{18}$ is Val or Nle; $R_{19}$ is CML, Leu, Ile, Ala or Aib; $R_{20}$ is Glu, D-Glu, Cys or His; $R_{21}$ is Nle or Met; $R_{22}$ is Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{33}$ is Lys, Orn or Cys; $R_{34}$ is Aib or Asn; $R_{39}$ is Glu or Asp; and $R_{41}$ is Ala or Ile; and wherein Thr, Leu-Thr or Asp-Leu-Thr can be optionally provided at the N-terminus; provided however that a second cyclizing bond may exist between $R_{20}$ and $R_{23}$.

Still another group of preferred CRF peptide antagonists are those having the formula or nontoxic salts thereof:

(cyclo 30-33)Y-D-Phe-$R_{13}$-Leu-Leu-Arg-$R_{17}$-$R_{18}$-Leu-$R_{20}$-Nle-$R_{22}$-$R_{23}$-$R_{24}$-$R_{25}$-$R_{26}$-Leu-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is Ac or hydrogen; $R_{13}$ is His, Tyr or Glu; $R_{17}$ is Glu or CML; $R_{18}$ is Val, Nle or Met; $R_{20}$ is His, Cys or Glu; $R_{22}$ is Ala, Aib, Thr, Asp or Glu; $R_{23}$ is Arg, Cys, Orn or Lys; $R_{24}$ is Ala or Aib; $R_{25}$ is Asp or Glu; $R_{26}$ is Gln, Asn or Lys; $R_{28}$ is Ala or Aib; $R_{29}$ is Gln, Aib or Glu; $R_{30}$ is Glu or Cys; $R_{31}$ is Ala or Aib; $R_{32}$ is His, Aib, Gly, Tyr or Ala; $R_{33}$ is Lys, Orn or Cys; $R_{34}$ is Asn or Aib; $R_{36}$ is Lys, Orn, Arg, Har or Leu; $R_{37}$ is CML, Leu or Tyr; $R_{39}$ is Glu, Aib or Asp; $R_{40}$ is Ile, Aib, Thr, Glu, Ala, Val, Leu, Nle, Phe, Nva, Gly or Gln; and $R_{41}$ is Ala, Ile, Gly, Val, Leu, Nle, Phe, Nva or Gln; and wherein Thr, Leu-Thr or Asp-Leu-Thr can be optionally provided at the N-terminus; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$.

A particularly preferred group of CRF antagonists are those having the formula or nontoxic salts thereof:

(cyclo 30-33)D-Phe-His-Leu-Leu-Arg-Glu-Val-Leu-Glu-Nle-Ala-$R_{23}$-Ala-Glu-Gln-Leu-Ala-Gln-$R_{30}$-Ala-His-$R_{33}$-Asn-Arg-Lys-Leu-Nle-Glu-Ile-Ile-$NH_2$ wherein $R_{23}$ is Arg or Lys; $R_{30}$ is Cys or Glu; $R_{33}$ is Cys, Lys or Orn; and wherein Thr, Leu-Thr or Asp-Leu-Thr can be optionally provided at the N-terminus; provided that when $R_{30}$ is Cys, $R_{33}$ is Cys and when $R_{30}$ is Glu, $R_{33}$ is Lys or Orn; or a nontoxic addition salt thereof. Two analogs of this group which are considered to be particularly biopotent from the standpoint of reducing high ACTH levels and raising blood pressure are:

cyclo(30-33)[D-Phe$^{12}$, Glu$^{30}$, Lys$^{33}$, Nle$^{21,38}$]rCRF(12-41), and cyclo(30-33)[D-Phe$^{12}$, Glu$^{30}$, Orn$^{33}$, Nle$^{21,38}$]rCRF(12-41).

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following formula:

$X^1$-D-Phe-$R_{13}$($X^7$ or $X^5$)-Leu-Leu-Arg($X^3$)-$R_{17}$($X^5$)-$R_{18}$-Leu-$R_{20}$($X^5$ or $X^8$)-Nle-$R_{22}$($X^2$ or $X^5$)-$R_{23}$($X^3$, $X^6$ or $X^8$)-$R_{24}$-$R_{25}$($X^5$)-$R_{26}$($X^4$ or $X^6$)-Leu-$R_{28}$-$R_{29}$($X^4$ or $X^5$)-$R_{30}$($X^5$ or $X^8$)-$R_{31}$-$R_{32}$($X^7$)-$R_{33}$($X^6$ or $X^8$)-$R_{34}$($X^4$)-Arg($X^3$)-$R_{36}$($X^3$ or $X^6$)-$R_{37}$($X^7$)-Nle-$R_{39}$ ($X^5$)-$R_{40}$($X^2$, $X^4$ or $X^5$)-$R_{41}$($X^4$)-$X^9$ wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl (Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The preferred alpha-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl (Xan), for the amido group of Asn or Gln. Asn or Gln is preferably coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

$X^6$ is hydrogen or a protecting group for the side chain amino substituent of Lys or Orn. Illustrative of suitable side chain amino-protecting groups are Z, 2-chlorobenzyloxycarbonyl(2Cl-Z), Tos, t-amyloxycarbonyl(Aoc), BOC and aromatic or aliphatic urethan-type protecting groups as specified hereinbefore. 2Cl-Z is preferred for a BOC strategy.

When His is present, $X^7$ is hydrogen or a protecting group for the imidazole nitrogen such as Tos or 2,4-dinitrophenyl (DNP), and when Tyr is present, $X^7$ is hydrogen or a protecting group for the hydroxyl group such as DCB. When Met is present, the sulfur may be protected, if desired, with oxygen.

$X^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group $X^6$, e.g. a base-labile group such as Fmoc; or a suitable labile protecting group for a carboxyl side chain which is removable without simultaneously removing the protecting group $X^5$, e.g., a base-labile group such as OFm (fluorenylmethyl ester); or is a direct bond between the residues in the 30- and 33-positions, e.g. when the cyclic form results from a carba or dicarba bond which is considered to be equivalent to a Cys-Cys bond.

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group such as an ester or an anchoring bond used in solid phase synthesis for linking to a solid resin support, preferably one represented by the formula:

-NH-benzhydrylamine (BHA) resin support and -NH-paramethylbenzhydrylamine (MBHA) resin support.

Cleavage from a BHA or MBHA resin directly gives the CRF analog amide. By employing a methyl-derivative of such a resin, a methyl-substituted amide can be created, which is considered to be the equivalent thereof.

In the formula for the intermediate, at least one of $X^1$, $X^2$, $X^3$, $X^4$, $X^5$, $X^6$, $X^7$ and $X^8$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

If an acyl group is present at the N-terminus, as represented by Y, acetyl (Ac), formyl (Fr), acrylyl (Acr) and benzoyl (Bz) are preferred.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$, (b) forming a cyclizing bond, particularly if one has not already been formed, (c) splitting off the protective group or groups or the anchoring bond from said peptide intermediate, (d) optionally forming a cyclizing bond, and (e) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to an MBHA resin.

Ile protected by BOC is coupled to the BHA resin using methylene chloride and dimethylformamide (DMF). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used, as described in Schroder & Lubke, "The Peptides", 1 pp 72–75 (Academic Press 1965) and in the well known Barany-Merrifield text.

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

Activating or coupling reagents for use in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1–27 (1970). P-nitrophenyl ester (ONp) can also be used to activate the carboxyl end of Asn or Gln for coupling. For example, BOC-Asn(ONp) can be coupled overnight using one equivalent of HOBt in a 50% mixture of DMF and methylene chloride.

Each protected amino acid or amino acid sequence is introduced into the solid phase reactor in about a threefold excess, and the coupling is carried out in a medium of dimethylformamide(DMF):$CH_2Cl_2$ (1:1) or in $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha- amino protecting group prior to the coupling of the next amino acid. The coupling reactions can be performed automatically, as on a BECKMAN 990 automatic synthesizer, using a program such as that reported in Rivier et al., *Biopolymers*, 1978, 17, pp.1927–1938.

After the desired amino acid sequence has been completed, the intermediate peptide is removed from the resin support unless it is desired to form the cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The cyclizing step for the CRF peptide analog depends, of course, upon the type of linkage which is desired between the residues in the 30- and 33-positions (and similarly for those in the 20- and 23-positions when a bi-cyclic molecule is being formed). When residues of L-Cys are included in both the 30- and 33-positions, it is often more convenient to carry out the cyclizing step following the cleavage from the resin and the removal of all of the protecting groups from the peptide. The cyclic form of the peptide is obtained by oxidization using a ferricyanide solution, preferably as described in Rivier et al., *Biopolymers*, Vol. 17 (1978), 1927–38, or by air oxidation, or in accordance with other known procedures.

To effect an amide cyclizing linkage (lactam bridge), cyclization may be carried out while the partially protected peptide remains attached to the resin as disclosed in U.S. Pat. Nos. 5,064,939 and 5,043,322, the disclosures of which are incorporated herein by reference. Such a procedure effectively creates an amide cyclizing bond between the two desired side chains while other residues, such as Asp, Glu and/or Lys, in the peptide intermediate retain their side-chain protection.

When cyclizing via an amide bond between a side-chain amino group of the 30-position residue and a side-chain carboxyl group of the 33-position residue, or vice-versa which is considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the 1-position residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. If 2 lactam bridges are to be incorporated in the molecule, the 30-33 bridge is preferably effected at a point in the synthesis prior to adding the 23-position residue, or a synthesis protocol such as taught in U.S. Pat. No. 5,064,939 is employed. Following cyclization, the peptide is completely deprotected and cleaved from the resin using a reagent, such as HF. Optionally a BOC-protecting group can be first removed using TFA.

Alternatively, cyclizations of peptides by such amide linkages can also be effected using teachings of U.S. Pat. Nos. 4,115,554, (Sep. 19, 1978); 4,133,805 (Jan. 9, 1979); 4,140,767 (Feb. 20, 1979); 4,161,521 (Jul. 17, 1979); 4,191,754 (Mar. 4, 1980); 4,238,481 (Dec. 9, 1980); 4,244,947 (Jan. 13, 1981); and 4,261,885 (Apr. 14, 1981).

The following Example I sets forth a preferred method for synthesizing CRF antagonists by the solid-phase technique.

EXAMPLE I

The synthesis of the (cyclo 30-33) [D-Phe$^{12}$, Glu$^{30}$, Lys$^{33}$, Nle$^{21,38}$]-human CRF(12-41) having the formula:

(cyclo 30–33)H—D—Phe—His—Leu—Leu—Arg—Glu—
Val—Leu—Glu—Nle—Ala—Arg—Ala—Glu—Gln—Leu—Ala—Gln—Glu—

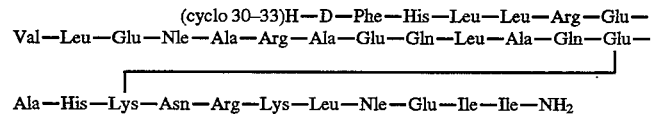

Ala—His—Lys—Asn—Arg—Lys—Leu—Nle—Glu—Ile—Ile—NH$_2$ is conducted in a stepwise manner on a MBHA hydrochloride resin, such as available from Bachem, Inc., having a substitution range of about 0.43 to 0.46 mequiv/gm resin. The synthesis is performed on an automatic BECKMAN 990B peptide synthesizer using a suitable program, preferably as follows:

| STEP | REAGENTS AND OPERATIONS | MIX TIMES MIN. |
|---|---|---|
| 1 | $CH_2Cl_2$ wash-80 ml. (2 times) | 1 |
| 2 | Methanol(MeOH) wash-30 ml. (2 times) | 1 |
| 3 | $CH_2Cl_2$ wash-80 ml. (3 times) | 1 |
| 4 | 50 percent TFA plus 5 percent 1,2-ethanedithiol in $CH_2Cl_2$-70 ml. (2 times) | 12 |
| 5 | Isopropanol wash-80 ml. (2 times) | 1 |
| 6 | TEA 12.5 percent in $CH_2Cl_2$-70 ml. (2 times) | 1 |
| 7 | MEOH wash-40 ml. (2 times) | 1 |
| 8 | $CH_2Cl_2$ wash-80 ml. (3 times) | 1 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |

Coupling of BOC-Ile results in the substitution of about 0.35 mmol. Ile per gram of resin. All solvents that are used are carefully degassed, preferably by sparging with an inert gas, e.g. helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser. BOC-Asn(Xan) or BOC-Gln(Xan) is coupled in the presence of one equivalent of DCC and two equivalents of HOBt in a 50% mixture of DMF and methylene chloride. Either 2Cl-Z or Fmoc is used as the protecting group for the Lys side chain depending upon whether it is to be part of a lactam bridge. Tos is used to protect the guanidino group of Arg and the imidazole group of His, and the side chain carboxyl group of Glu is protected by OChx or OFm depending upon whether it is to take part in the cyclizing reaction. At the end of the synthesis, the following composition is obtained:

BOC-D-Phe-His(Tos)-Leu-Leu-Arg(Tos)-Glu(OChx)-Val-Leu-Glu(OChx)-Nle-Ala-Arg(Tos)-Ala-Glu(OChx)-Gln(Xan)-Leu-Ala-Gln(Xan)-Glu(OFm)-Ala-His(Tos)-Lys (Fmoc)-Asn(Xan)-Arg(Tos)-Lys(2Cl-Z)-Leu-Nle-Glu(OChx)-Ile-Ile-MBHA resin support.

Next cyclization (lactamization) of residues 30 and 33 is performed by the method referred to hereinbefore and described more fully as follows. After washes with dichloromethane (DCM) (2x) and dimethylformamide (DMF) (2x), the OFmc/Fmoc groups of $Glu^{30}$ and $Lys^{33}$, respectively, are removed by 20% piperidine in DMF (1x1 min. and 2x10 min.), followed by washing with (DMF) (2x), methanol (MeOH) (2x) and dichloromethane (DCM) (2x). The peptide-resin is cyclized by reaction at room temperature with threefold excess of benzotriazol-1-yl-oxy-tris (dimethylamino)phosphonium hexafluorophosphate (BOP) in presence of excess diisoproplyethylamine (DIEA) in dimethylformamide (DMF). After washing, the cyclization is repeated two more times for four hours and then once for twelve hours. The reaction is followed by Kaiser ninhydrin test (E. Kaiser et al., *Color test for detection of free terminal amino groups in the solid-phase synthesis of peptides, Anal Biochem* (1970) 34:595–98) and in general is complete after 24 hours.

After removal of the $N^\alpha$-BOC protecting group, the fully protected peptide-resin is dried. About 2 grams is cleaved by anhydrous HF (20 mL) in the presence of anisole (0.6 mL) at 0° C. for 90 min. The crude peptide is precipitated and washed with anhydrous diethyl ether (450 mL in 3 portions), filtered, extracted from the resin with 380 mL (r portions) of 0.1% TFA in $CH_3CN/H_2O$ (60:40) and lyophilized to give the crude product.

The crude lyophilized peptide is purified by preparative reverse-phase HPLC (RHPLC) on a system composed of a WATERS ASSOCIATES (Milford, Mass.) PREP LC 3000 System, a WATERS ASSOCIATES 600E System Controller, a Shimadzu SPD-6A UV Spectrophotometric variable-wavelength detector (detection was 230 nm), WATERS 1000 PrepPak Module, and a FISHER (Lexington, Mass.) RECORDALL Series 5000 strip chart recorder (chart speed 0.25 cm/min.). Final peptide purification is carried out in two steps using buffers of TEAP pH 2.25 and 0.1% TFA.

The crude peptide is first dissolved in 400 mL buffer A: triethylammonium phosphate (TEAP) (pH 2.25) (1:4 v/v), loaded on a preparative reversed phase HPLC cartridge (5×30 cm) packed in the laboratory using WATERS polyethylene sleeves and frits and VYDAC $C_{18}$ silica gel (The Separations Group, Hesperia, Calif.; 300Å pore size, 15 to 20-µm particle size). The peptide is eluted using buffer B: 60% $CH_3CN$ in buffer A with a gradient from 30 to 60% B. Buffers A (triethlyammonium phosphate (TEAP), pH 2.25) and B ($CH_3CN$ in A) are pumped at a flow rate of 95 mL/min for 90 minutes. Fractions containing a total of 50–100 mL are screened under Isocratic conditions (61% B, retention time about 2.84 min.), and fractions containing the compound are identified and pooled.

In the second step, the pooled fractions are diluted with 160 mL of $H_2O$ and eluted by using as buffer A: 0.1% TFA/$H_2O$ and B: 0.1% TFA in $CH_3CN/H_2O$ (60:40), with a gradient from 40 to 70% B in 90 minutes (retention time about 67 min.). Fractions containing a total of 30–50 mL are screened, fractions containing the compound are pooled and lyophilized to yield the final product peptide.

Specific optical rotation at the Sodium D line of the peptide synthesized and purified in this manner is measured on a PERKIN ELMER Model 241 Polarimeter as
$[\alpha]_D^{22} = -62.4° \pm 1.0$ (c=1 in 1% acetic acid)
(without correction for the presence of $H_2O$ and TFA); it has a purity of about 98%. Purity is further confirmed by mass spectroscopy (MS) and capillary zone electrophoresis (CZE).

Amino acid analysis of the peptide [after 4 N methanesulfonic acid hydrolysis at 110° C. for 24 h] is performed on a PERKIN ELMER LC system (Norwalk, Conn.) comprising of two Series 10 LC pumps, an ISS-100 sample injector, an RTC 1 column oven, a KRATOS SPECTROFLOW 980 fluorescence detector, and an LCI-100 integrator. A PIERCE AA511 ion-exchange column is maintained at 60° C., and post-column derivatization with o-phthalaldehyde is performed at 52° C. Samples containing the internal standard γ-aminobutyric acid are injected and, 5 minutes after injection, are subjected to a gradient of 0 to 100% B for 25 minutes and then 100% B for 15 minutes. The flow rate is 0.5 mL/min, and A and B buffers are PIERCE PICO buffer (pH 2.20) and BECKMAN MICROCOLUMN sodium citrate buffer (pH4.95), respectively. This analysis gives the expected amino acid ratios.

The synthesis is repeated without the cyclization step to produce the comparable linear peptide.

In vitro biopotency of the product peptide can be measured as follows. Rat anterior pituitary glands from male Sprague-Dawley rats are dissociated by collagenase and plated (0.16×$10^6$ cells/well in 48-well plates) in medium containing 2% fetal bovine serum (FBS). Three days after plating, the cells are washed three times with fresh medium containing 0.1% bovine serum albumin (BSA) and incubated for 1 hour. Following the 1 hour preincubation, the cells are washed once more, and the test peptides are applied in the presence of 1 nM oCRF. At the end of a 3 hour incubation period the media are collected and the level of ACTH is determined by radioimmunoassay (Diagnostic Products Corporation). The peptide product of the above described synthesis exhibits biopotency about 42 times (4200%) that of the present "standard" peptide, [D-Phe$^{12}$, Nle$^{21,38}$]rCRF(12-41). The linear peptide exhibits a biopotency of only about 10% of that of the standard.

Administration of the peptide inhibits the secretion of ACTH and βendorphin-like immuno-activities (β-END-LI) and exhibits especially long duration of inhibition. The in vivo assays which are employed to test these CRF antagonists use adrenalectomized (ADX) rats. Adult male Sprague Dawley rats (230–250 g) are adrenalectomized via a lombar approach under halothane anesthesia. Their diet is supplemented with 0.9% NaCl in the drinking water and with oranges. Two days prior to the experiments, the animals are equipped with jugular cannulae, as described in C. Rivier, et al., *Endocrinology*, 110, 272–278 (1982). On the morning of the experiments, the i.v. cannulae are connected to a line filled with heparinized saline, and the rats are placed in individual buckets and left undisturbed for 2 hours. For the experiment, a first blood sample of 0.3 mL is withdrawn, the test solution is injected (in an 0.2–0.5 mL volume), and subsequent blood samples are obtained at about 15, 45, 90 and 120 minutes. The blood samples are centrifuged, and the separated plasma are kept frozen (–20° C.) until assayed for ACTH values. Plasma ACTH levels are measured as described in C. Rivier, et al. *J. Neuroscience*, 14, 1985 (1994).

As a result of in vivo testing at a level of 1 mg/kg of body weight, it is shown that, at 15 minutes time, the cyclic CRF antagonist is more effective than the standard CRF antagonist in reducing ACTH levels in the serum. At 45 minutes following injection, the cyclic compound depresses the ACTH levels even further than at the 15 minute level, while the effect of the standard CRF antagonist has run its course and levels are substantially the same as in the control animals. At 90 minutes, the ACTH levels remain at about this low level for those rats treated with the cyclic compound, well below the level of the control rats and those treated with the standard CRF antagonist. At 120 minutes following injection, the level of ACTH is essentially back to normal. When tested at levels of 0.3 mg/kg of body weight, the results are essentially the same for 15 and 45 minutes; however, at 90 minutes, there is still some improvement over the rats treated with the standard CRF antagonist but it is not as significant as shown when injected at a level of 1 milligram per kg of body weight. One further series of tests is carried out where rats are injected with the standard CRF antagonist at a level of 3 mg/kg and 2 sets of other rats are injected with the cyclic CRF antagonists at levels of 0.1 mg/kg and 0.03 mg/kg. The results are essentially the same as in the previous two tests at 15 and 45 minutes, with even the 0.03 mg/kg injection showing a significant improvement over the 3 mg/kg injection of the standard CRF antagonist. At 90 minutes, there is still some marginal improvement over the rats injected with the 3 mg/kg of the standard; however, the ACTH levels essentially return to about the levels at the beginning of the test upon the passage of 90 minutes. The tests show that, even when used at a level 1/100 of the amount of the standard CRF antagonist, the cyclic compound still performs substantially better over a 45 minute time span.

EXAMPLE IA

The synthesis of Example I is repeated, substituting D-Tyr for D-Phe, to produce the following peptide:

(cyclo 30-33)[D-Tyr$^{12}$, Nle$^{21,38}$, Glu$^{30}$, Lys$^{33}$]-rCRF.

Specific optical rotation at the Sodium D line of the peptide is measured, as previously described, as $[\alpha]_D^{22}$=–59.0°±1.0 (c=1 in 1% acetic acid, without correction for the presence of H$_2$O and TFA). It has a purity of about 98%, further confirmed by mass spectroscopy (MS) and capillary zone electrophoresis. The peptide's biopotency, determined as previously described, is about 6.5 times that of the standard peptide, [D-Phe$^{12}$, Nle$^{21,38}$]rCRF (12-41).

EXAMPLE II

The synthesis of (cyclo 30-33) [D-Phe$^{12}$, Nle$^{21,38}$, Glu$^{30}$, Orn$^{33}$]-human CRF(12-41) having the formula:

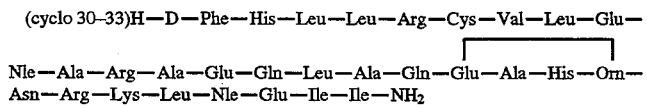

is conducted as described in Example I above, except that residue 33 is Orn instead of Lys. Administration of the peptide inhibits the secretion of ACTH and β-END-LI.

EXAMPLE IIA

The synthesis of (bicyclo 20-23, 30-33) [D-Phe$^{12}$, Nle$^{21,38}$, Lys$^{23,33}$, Glu$^{30}$]-human CRF(12-41) having the formula:

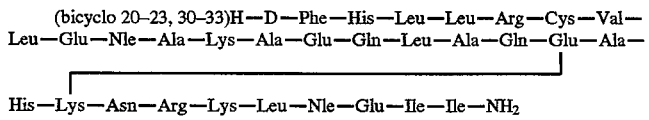

is conducted as generally described in Example I above, except that the lactam bridge between residues 30 and 33 is completed before residue 23 is added to the peptide-resin.

Administration of the peptide inhibits the secretion of ACTH and β-END-LI.

EXAMPLE III

The peptide of (cyclo 30-33) [D-Phe$^{12}$, Nle$^{21,38}$, Cys$^{30,33}$]-human CRF(12-41) having the formula:

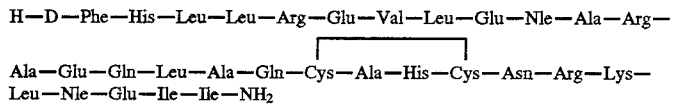

is synthesized.

The synthesis protocol previously described herein is employed to produce the fully protected peptide-resin which is cleaved by HF. After precipitation and washing with diethyl ether (480 mL in 3 portions), the peptide is extracted with water (200 mL) and 5.0% AcOH (100 mL). The resulting solution is poured into 4.0 L of degassed water and the pH adjusted to 6.8–7.0 with NH$_4$OH. As the mixture becomes cloudy, CH$_3$CN (300 mL) is added to avoid precipitation. The mixture is then stirred at 4° C. under air atmosphere, and after 48 h, cyclization is complete (Ellman test). The pH is adjusted to 5.0 with AcOh, and the resulting solution is loaded on a Bio-Rex-70 column (120 mL). The column is washed with 0.5% AcOH (200 mL), and the peptide elutes with 50% AcOH. Fractions are collected, and those containing ninhydrin-positive material are diluted and lyophilized (80 mg).

Purification is performed in three steps. First the peptide is dissolved in buffer A (TEAP pH 2.25, 300 mL) and eluted by using as buffer B: 60% CH$_3$CN in A, with a gradient from 30 to 60% B in 60 minutes. Fractions are screened under isocratic conditions (53% B) and fractions containing the compound are pooled. In the second step, the pooled fractions are diluted with H$_2$O and eluted using buffer A: TEAP (pH 6.0) and B: 60% CH$_3$CN in A, with a gradient from 30 to 55% B in 60 minutes. Fractions are again screened under isocratic conditions (53% B), and the pooled fractions are diluted with H$_2$O and eluted using buffer A: 0.1% TFA/H$_2$O and B: 0.1% TFA in CH$_3$CN/H$_2$O (60:40), with a gradient from 30 to 60% B in 20 minutes. The fractions containing the product are pooled and lyophilized to yield the product peptide.

Administration of the peptide inhibits the secretion of ACTH and β-END-LI.

EXAMPLE IV

Using the procedure as generally set forth in Example I, the following peptides are also prepared which are CRF antagonists:

| | |
|---|---|
| (c 30-33) | [D-Phe$^{12}$, Nle$^{21,38}$, Glu$^{30}$, Lys$^{33}$]-AHC(9-41) |
| " | [Glu$^{30}$, Lys$^{33}$, Aib$^{34}$]-AHC(12-41) |
| " | [D-Phe$^{12}$, Glu$^{30}$, Lys$^{33}$]-oCRF(10-41) |
| " | [Glu$^{30}$, Lys$^{33}$, Nle$^{21,38}$]-rCRF(12-41) |
| " | [D-Phe$^{12}$, Glu$^{30}$, Lys$^{33}$]-oCRF(12-41) |
| " | [Nle$^{18,21}$, Glu$^{30}$, Lys$^{33}$]-AHC(10-41) |
| " | [D-Phe$^{12}$, Glu$^{30}$, Lys$^{33}$]-rCRF(12-41) |
| " | [D-Phe$^{12}$, Nle$^{21}$, Glu$^{30}$, Lys$^{33}$, Aib$^{34}$]-oCRF(12-41) |
| " | [D-Phe$^{12}$, Glu$^{30}$, Lys$^{33}$]-AHC(12-41) |
| " | [D-Phe$^{12}$, Nle$^{21,38}$, Aib$^{22}$, Glu$^{30}$, Lys$^{33}$]-rCRF(12-41) |
| " | [D-Phe$^{12}$, Nle$^{21,38}$, Aib$^{24}$, Glu$^{30}$, Lys$^{33}$]-rCRF(12-41) |
| " | [D-Phe$^{12}$, Nle$^{21,38}$, Aib$^{28}$, Glu$^{30}$, Lys$^{33}$]-rCRF(12-41) |
| " | [D-Phe$^{12}$, Nle$^{21,38}$, Aib$^{29}$, Glu$^{30}$, Lys$^{33}$]-rCRF(12-41) |
| " | [D-Phe$^{12}$, Nle$^{21,38}$, Glu$^{30}$, Aib$^{31}$, Lys$^{33}$]-rCRF(12-41) |
| " | [D-Phe$^{12}$, Nle$^{21,38}$, Glu$^{30}$, Aib$^{32}$, Lys$^{33}$]-rCRF(12-41) |
| " | [D-Phe$^{12}$, Nle$^{21,38}$, Glu$^{30}$, Lys$^{33}$, Aib$^{34}$]-rCRF(12-41) |
| " | [D-Phe$^{12}$, Nle$^{21,38}$, Glu$^{30}$, Lys$^{33}$, Aib$^{39}$]-rCRF(12-41) |
| " | [D-Phe$^{12}$, Nle$^{21,38}$, Glu$^{30}$, Lys$^{33}$, Aib$^{40}$]-rCRF(12-41) |
| " | [Nle$^{18,21}$, Glu$^{30}$, D-His$^{32}$, Lys$^{33}$]-AHC(11-41) |
| " | [D-Phe$^{12}$, Glu$^{30}$, Lys$^{33}$, Aib$^{34}$]-rCRF(12-41) |
| " | [Nle$^{21,38}$, Glu$^{30}$, Lys$^{33}$]-rCRF(10-41) |
| " | [D-Tyr$^{12}$, Nle$^{21,38}$, Glu$^{30}$, Lys$^{33}$, Aib$^{39}$]-oCRF(9-41) |
| " | [Nle$^{21,38}$, Glu$^{30}$, D-His$^{32}$, Lys$^{33}$]-rCRF(9-41) |
| " | [D-4ClPhe$^{12}$, Nle$^{18,21}$, Aib$^{22}$, Glu$^{30}$, Lys$^{33}$]-AHC(12-41) |
| " | [Tyr$^{13}$, Nle$^{21}$, Glu$^{30}$, Lys$^{33}$, CML$^{37}$]-oCRF(11-41) |
| " | [CML$^{17}$, Nle$^{21,38}$, Glu$^{30}$, Lys$^{33}$, CML$^{37}$]-oCRF(10-41) |
| " | [D-3Pal$^{12}$, Nle$^{21,38}$, Aib$^{24}$, Glu$^{30}$, Lys$^{33}$, CML$^{37}$]-oCRF(12-41) |

These peptides are biopotent in inhibiting the secretion of ACTH and β-END-LI in response to various stimuli.

EXAMPLE V

Using the procedure as generally set forth in Example I, the following peptides are also prepared which are CRF antagonists:

| | |
|---|---|
| (c 30-33) | [CML$^{17}$, Glu$^{30}$, Lys$^{33}$]-AHC(12-41) |
| " | [CML$^{17}$, Glu$^{30}$, Lys$^{33}$]-oCRF(10-41) |
| " | [D-Phe$^{12}$, CML$^{14}$, Nle$^{21,38}$, Glu$^{30}$, Lys$^{33}$]-rCRF(12-41) |
| " | [D-2Nal$^{12}$, CML$^{14}$, Glu$^{30}$, Lys$^{33}$]-oCRF(12-41) |
| " | [CML$^{17}$, Nle$^{18,21}$, Glu$^{30}$, Lys$^{33}$]-AHC(10-41) |
| " | [D-Phe$^{12}$, CML$^{17}$, Glu$^{30}$, Lys$^{33}$]-rCRF(12-41) |
| " | [D-Phe$^{12}$, CML$^{17,37}$, Nle$^{21}$, Glu$^{30}$, Lys$^{33}$]-oCRF(12-41) |
| " | [D-4ClPhe$^{12}$, CML$^{15}$, Glu$^{30}$, Lys$^{33}$]-AHC(12-41) |
| " | [D-Phe$^{12}$, CML$^{15}$, Nle$^{21,38}$, Glu$^{30}$, Lys$^{33}$]-rCRF(12-41) |
| " | [D-Phe$^{12}$, CML$^{17}$, Nle$^{21,38}$, Glu$^{30}$, Lys$^{33}$]-rCRF(12-41) |
| " | [D-Phe$^{12}$, CML$^{17,37}$, Nle$^{21,38}$, Glu$^{30}$, Lys$^{33}$]-rCRF(12-41) |
| " | [Nle$^{18,21}$, CML$^{17,37}$, Glu$^{30}$, D-His$^{32}$, Lys$^{33}$]-AHC(11-41) |
| " | [D-Phe$^{12}$, CML$^{17,37}$, Glu$^{30}$, Lys$^{33}$, Aib$^{34}$]-rCRF(12-41) |
| " | [CML$^{17,37}$, Nle$^{21,38}$, Glu$^{30}$, Lys$^{33}$]-rCRF(10-41) |
| " | [D-Phe$^{12}$, CML$^{19}$, Glu$^{30}$, Lys$^{33}$]-rCRF(12-41) |
| " | [D-Pal$^{12}$, Nle$^{21}$, CML$^{27,37}$, Glu$^{30}$, Lys$^{33}$]-oCRF(12-41) |
| " | [D-Tyr$^{12}$, CML$^{27}$, Glu$^{30}$, Lys$^{33}$]-AHC(12-41) |
| " | [D-Phe$^{12}$, CML$^{19}$, Nle$^{21,38}$, Glu$^{30}$, Lys$^{33}$]-rCRF(12-41) |
| " | [D-Phe$^{12}$, Nle$^{21,38}$, CML$^{27}$, Glu$^{30}$, Lys$^{33}$]-rCRF(12-41) |
| " | [D-Phe$^{12}$, CML$^{19,37}$, Nle$^{21,38}$, Lys$^{23}$, Glu$^{30}$, Lys$^{33}$]-rCRF(12-41) |

These peptides are biopotent in inhibiting the secretion of ACTH and β-END-LI in response to various stimuli.

A cyclizing bond between the residues in the 30- and 33-positions is also valuable to enhance the properties of CRF agonists. These agonists, as well known in the art, can include the entire 41-residue peptide or can be shortened at the N-terminus by deleting a sequence of 3 residues or as many as 5 residues, if desired. Any of the cyclizing bonds disclosed hereinbefore with regard to the CRF antagonists can be employed; however, a lactam bond between residues having a carboxyl side chain in the 30-position and an amino side chain in the 33-position is preferred. The N-terminus of these CRF agonists can be acylated by acylating agents as known in the art generally having from 1 to 7 carbon atoms, such as acetyl, acrylyl and benzoyl.

The following Example sets forth the preferred method for synthesizing CRF agonists by the solid-phase technique.

EXAMPLE VI

The synthesis of (cyclo 30-33)[Ac-Pro$^4$, D-Phe$^{12}$, Nle$^{21, 38}$, Glu$^{30}$, Lys$^{33}$]-rCRF(4-41) having the formula:

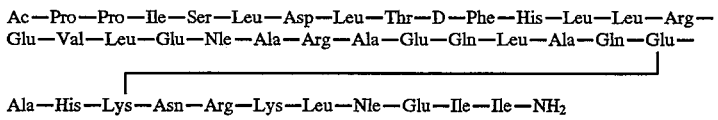

is conducted in a stepwise manner on a MBHA hydrochloride resin, such as available from Bachem, Inc., having a substitution range of about 0.1 to 0.5 mmoles/gm. resin. The synthesis is performed on an automatic BECKMAN 990B peptide synthesizer using a suitable program, preferably as follows:

| STEP | REAGENTS AND OPERATIONS | MIX TIMES MIN. |
|---|---|---|
| 1 | CH$_2$Cl$_2$ wash-80 ml. (2 times) | 1 |
| 2 | Methanol(MeOH) wash-30 ml. (2 times) | 1 |
| 3 | CH$_2$Cl$_2$ wash-80 ml. (3 times) | 1 |
| 4 | 50 percent TFA plus 5 percent 1,2-ethane-dithiol in CH$_2$Cl$_2$-70 ml. (2 times) | 12 |
| 5 | Isopropanol wash-80 ml. (2 times) | 1 |
| 6 | TEA 12.5 percent in CH$_2$Cl$_2$-70 ml. (2 times) | 1 |
| 7 | MEOH wash-40 ml. (2 times) | 1 |
| 8 | CH$_2$Cl$_2$ wash-80 ml. (3 times) | 1 |
| 9 | Boc-amino acid (10 mmoles) in 30 ml. of either DMF or CH$_2$Cl$_2$, depending upon the solubility of the particular protected amino acid, (1 time) plus DCC (10 remoles) in CH$_2$Cl$_2$ | 30–300 |

Coupling of BOC-Ile results in the substitution of about 0.35 mmol. Ile per gram of resin. All solvents that are used are carefully degassed, preferably by sparging with an inert gas, e.g., helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain unless the Lys residue is to take part in the lactam bridge when Fmoc is used. Tos is used to protect the guanidino group of Arg and the imidazole group of His, and the side-chain carboxyl group of Glu or Asp is protected by OBzl except for Glu$^{30}$ which is protected by OFm. At the end of the synthesis, the following composition is obtained:

BOC-Pro-Pro-Ile-Ser(Bzl)-Leu-Asp(OBzl)-Leu-Thr(Bzl)-D-Phe-His(Tos)-Leu-Leu-Arg(Tos)-Glu(OBzl)-Val-Leu-Glu(OBzl)-Nle-Ala-Arg(Tos)-Ala-Glu(OBzl)-Gln(Xan)-Leu-Ala-Gln(Xan)-Glu(OFm)-Ala-His(Tos)-Lys(Fmoc)-Asn(Xan)-Arg(Tos)-Lys(2-Cl-Z)-Leu-Nle-Glu(OBzl)-Ile-Ile-resin support. Xan may have been partially or totally removed by TFA treatment used to deblock the alpha-amino protecting group.

Next cyclization (lactamization) of residues 30 and 33 is performed by the method referred to hereinbefore and described more fully as follows. After washes with dichloromethane (DCM) (2x) and dimethylformamide (DMF) (2x), the OFm/Fmoc groups of Glu$^{30}$ and Lys$^{33}$, respectively, are removed by 20% piperidine in DMF (1×1 min. and 2×10 min.), followed by washing with (DMF) (2x), methanol (MeOH) (2x) and dichloromethane (DCM) (2x). The peptide-resin is cyclized by reaction at room temperature with threefold excess of benzotriazol-1-yl-oxy-tris(dimethylamino)phosphonium hexafluorophosphate (BOP) in presence of excess diisoproplyethylamine (DIEA) in dimethylformamide (DMF). After washing, the cyclization is repeated two more times for four hours and then once for twelve hours. The reaction is followed by Kaiser ninhydrin test (E. Kaiser et al., *Color test for detection of free terminal amino groups in the solid-phase synthesis of peptides, Anal Biochem* (1970) 34:595–98) and in general is complete after 24 hours.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one-half hour. After elimination of the HF under high vacuum, the resin-peptide is washed alternately with dry diethyl ether and chloroform, and the peptides are then extracted with de-gassed 2N aqueous acetic acid and separated from the resin by filtration.

The peptide is purified by gel permeation followed by preparative HPLC as described in Marki, et al., *J. Am. Chem. Soc.*, 103, 3178 (1981); Rivier, et al., *J. Chromatography*, 288, 303–328 (1984); and Hoeger, et al., *BioChromatography*, 2, 3, 134–142 (1987). The chromatographic fractions are carefully monitored by HPLC, and only the fractions showing substantial purity are pooled.

To check whether the precise sequence is achieved, the rCRF analog is hydrolyzed in sealed evacuated tubes containing constant boiling HCl, 3 µl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 38-residue peptide structure has been obtained.

Specific optical rotation of the h/rCRF peptide, synthesized and purified in the foregoing manner, is measured on a PERKIN ELMER Model 241 Polarimeter as $[\alpha]_D^{22}$=−38.9±1.0 (c=1 in 9% acetic acid without correction for the presence of H$_2$O and TFA); it has a purity of about 96%.

The peptide is judged to be homogeneous using thin layer chromatography and several different solvent systems. It is specifically subjected to reversed-phase high performance liquid chromatography using a Waters HPLC system with a 0.46×25 cm. column packed with 5 µm C$_{18}$ silica, 300Å pore size. Buffer A which is used is an aqueous 0.1% trifluoroacetic acid solution consisting of 1.0 ml. of TFA per 1000 ml. of solution; Buffer B is 100% acetonitrile. The determination is run at room temperature with a gradient from 15.5% Buffer B to 71.5% Buffer B over 30 minutes. The flow rate is 1.8 ml. per minute, and the retention time is 23.4 minutes.

The peptide is judged to be homogeneous using thin layer chromatography and several different solvent systems. It is specifically subjected to reversed-phase high performance liquid chromatography using a WATERS HPLC system with a 0.46×25 cm. column packed with 5 μm $C_{18}$ silica, 300Å pore size. Amino acid analysis of the resultant, purified peptide is carried out and found to be consistent with the formula for the prepared peptide, confirming that the 38-residue peptide structure is obtained.

The cyclic synthetic CRF agonist is examined for its effects on the secretion of ACTH and β-endorphin in vitro and also in vivo. Its potency to stimulate the secretion of ACTH and β-endorphin by cultured rat pituitary cells is measured using the procedure as generally set forth in *Endocrinology*, 91, 562 (1972) and compared against synthetic oCRF. It is found to be about 6 times as potent as the native hormone. In vivo testing is carried out using the general procedure set forth in C. Rivier et al., *Science*, 218, 377 (1982) and shows a significant lowering of blood pressure when administered peripherally.

The synthesis is repeated without the cyclization step to produce the comparable linear peptide. In vitro testing shows that it is about 4.5 times as potent as the native hormone.

EXAMPLE VII

The peptide (cyclo 30-33)[D-Phe$^{12}$, Nle$^{21,38}$, Glu$^{30}$, Orn$^{33}$]-rCRF(3-41) having the formula:

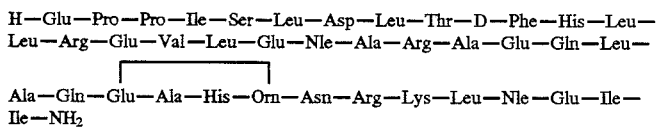

is synthesized. Amino acid analysis of the resultant, purified peptide is consistent with the formula for the prepared peptide and confirms that the 39-residue peptide structure is obtained. Testing in accordance with the general procedure set forth in Example VI shows that it likewise stimulates the secretion of ACTH and β-END-LI and causes a very significant lowering of blood pressure when administered peripherally.

EXAMPLE VIII

The peptide [D-Phe$^{12}$, Nle$^{21,38}$, Glu$^{30}$, Lys$^{33}$]-oCRF having the formula:

H-Ser-Gln-Glu-Pro-Pro-Ile-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Glu-Ala-His-Lys-Asn-Arg-Lys-Leu-Nle-Asp-Ile-Ala-NH$_2$ is synthesized using a procedure generally as set forth in Example VI. Amino acid analysis of the resultant, purified peptide is consistent with the formula for the prepared peptide and confirms that the 41-residue peptide structure is obtained. Testing in accordance with the general procedure set forth hereinbefore shows that it likewise stimulates the secretion of ACTH and β-END-LI and causes a very significant lowering of blood pressure when administered peripherally.

EXAMPLE IX

Using the procedure set forth in Example VI, the following peptides are also prepared:

| | |
|---|---|
| (c 30–33) | [Acetyl-Ser$^1$, D-Phe$^{12}$, Nle$^{21,38}$, Glu$^{30}$, Lys$^{33}$]-rCRF |
| " | [D-Phe$^{12}$, Glu$^{30}$, Lys$^{33}$]-oCRF |
| " | [D-Phe$^{12}$, D-Ala$^{24}$, Glu$^{30}$, Lys$^{33}$]-rCRF(4-41) |
| " | [D-Phe$^{12}$, Nle$^{21}$, Aib$^{34}$, Glu$^{30}$, Lys$^{33}$]-oCRF |
| " | [Formyl-Ser$^1$, D-Phe$^{12}$, Nle$^{21,38}$, Glu$^{30}$, Lys$^{33}$]-rCRF |
| " | [CML$^{17,37}$, Glu$^{30}$, Lys$^{33}$]-oCRF |
| " | [D-Tyr$^{12}$, CML$^{17}$, Glu$^{30}$, Lys$^{33}$]-rCRF(2-41) |
| " | [D-3Pal, Nle$^{21,38}$, Glu$^{30}$, Lys$^{33}$]-oCRF |
| " | [Glu$^{30}$, D-His$^{32}$, Lys$^{33}$, Aib$^{34}$]-oCRF |
| " | [D-Phe$^{12}$, D-Ala$^{24}$, Glu$^{30}$, D-His$^{32}$, Lys$^{33}$]-rCRF(6-41) |
| " | [Nle$^{21}$, Aib$^{29}$, Glu$^{30}$, D-His$^{32}$, Lys$^{33}$]-oCRF |
| " | [Acrylyl-Glu$^2$, Nle$^{21,38}$, Glu$^{30}$, D-His$^{32}$, Lys$^{33}$]-rCRF(2-41) |
| " | [Nle$^{18,21}$, Glu$^{30}$, D-His$^{32}$, Lys$^{33}$]-AHC |
| " | [D-Pro$^4$, D-Phe$^{12}$, Nle$^{18,21}$, Glu$^{30}$, Lys$^{33}$]-AHC(4-41) |
| " | [D-Tyr$^3$, Nle$^{18}$, Nva$^{21}$, Glu$^{30}$, Lys$^{33}$]-AHC |
| " | [CML$^{17}$, Nle$^{18,21}$, Glu$^{30}$, Lys$^{33}$]-AHC |
| " | [D-Phe$^{12}$, CML$^{17}$, Glu$^{30}$, Lys$^{33}$]-AHC |
| " | [D-4ClPhe$^{12}$, Glu$^{30}$, Lys$^{33}$, CML$^{37}$]-AHC |
| " | [Nle$^{18,21}$, Glu$^{30}$, Lys$^{33}$, CML$^{37}$]-AHC |
| " | [CML$^{17}$, Glu$^{30}$, Lys$^{33}$]-AHC |
| " | [Tyr$^{13}$, Glu$^{30}$, Lys$^{33}$]-AHC |
| " | [Aib$^{19}$, Nle$^{21}$, Glu$^{30}$, Lys$^{33}$, CML$^{37}$]-oCRF |
| " | [D-2Nal$^{12}$, Nle$^{21,38}$, Aib$^{29}$, Glu$^{30}$, Lys$^{33}$, CML$^{37}$]-oCRF |
| " | [Nle$^{21,38}$, Glu$^{30}$, Lys$^{33}$, CML$^{37}$]-oCRF |

These peptides are biopotent in stimulating the secretion of ACTH and β-END-LI and decreasing systemic blood pressure when administered intravenously.

CRF profoundly stimulates the pituitary-adrenalcortical axis, and CRF agonists should be useful to stimulate the functions of this axis in some types of patients with low endogenous glucocorticoid production. For example, CRF agonists should be useful in restoring pituitary-adrenal function in patients having received exogenous glucocorticoid therapy whose pituitary-adrenalcortical functions remain suppressed. CRF antagonists should be useful to inhibit the functions of this axis in some types of patients with high ACTH and endogenous glucocorticoid production. For example, CRF antagonists may be useful in regulating pituitary-adrenal function in patients having pituitary cushings disease or any CRF-sensitive tumor.

Most other regulatory peptides have been found to have effects upon the endocrine system, the central nervous system and upon the gastrointestinal tract. Because ACTH and β-END-LI secretion is the "sine qua non" of mammal's response to stress, it was not surprising that CRF has significant effects on the brain as a mediator of many of the body's stress responses. Accordingly, CRF antagonists delivered to the brain should also find application in modifying the mood, learning and behavior, e.g. drug addition and drug and alcohol withdrawal, of normal and mentally disordered individuals. Furthermore, CRF antagonists in the brain could ameliorate stress-induced conditions to which endogenous CRF might contribute, including some types of hypertension, anorexia nervosa, hemorrhagic stress, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function. They may also be used to treat HIV infections and Alzheimer's disease.

All CRF-related peptides have been shown to dilate the mesenteric vascular bed. CRF antagonists may also be of use for decreasing blood flow to the gastrointestinal tract of mammals, particularly humans. Also, CRF influences gastric acid production, and CRF antagonists are expected to also be effective to modulate gastrointestinal functions, including abdominal bowel syndrome and inflammatory diseases.

CRF antagonists or the nontoxic addition salts thereof, combined with a pharmaceutically acceptable carrier to form a pharmaceutical composition, may be administered to mammals, including humans, either intravenously, subcutaneously, intramuscularly, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous glucocorticoid production or for possible uses outlined above. Administration may be in a variety of dosage forms such as tablets, lozenges, powders, syrups, injectable solutions and the like. The required dosage will vary with the particular condition being treated, with the severity of the condition and with the duration of desired treatment, and multiple dosages may be used for a single day. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found. For parental administration, solutions in peanut oil, in aqueous propylene glycol, or in sterile aqueous solution may be employed. Such aqueous solutions, which are suitably buffered, are especially suitable for intravenous, intramuscular, subcutaneous and intraperitoneal administration. Sterile aqueous media are readily available.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, hydriodide, cinnamate, sulphate, sulfamate, sulfonate, phosphate, tannate, oxalate, fumarate, gluconate, alginate, maleate, acetate, citrate, benzoate, succinate, malate, ascorbate, tartrate and the like which can be prepared in a conventional manner. If the active ingredient is to be administered in tablet form, the tablet may contain a binder or excipient, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician in single or multiple doses, and pharmaceutical compositions will usually contain the peptide in conjunction with a conventional, pharmaceutically-acceptable carrier. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal. For the treatment of inflammatory diseases about 0.1 to about 100 mg/kg is generally employed; for gastrointestinal diseases about 0.1 to about 50 mg/kg, as well as for anorexia nervosa, hemorrhagic stress, treatment of drug and alcohol withdrawal symptoms and treatment of fertility problems. The daily dosage may be given in a single dose or up to three divided doses.

As used herein all temperatures are ° C. and all ratios are by volume. Percentages of liquid materials are also by volume.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the antagonists. Instead of D-Phe at the N-terminus, L-Phe or another appropriate D-isomer generally similar to those hereinbefore mentioned may be present and are considered to be equivalent. The N-terminus of rCRF(12-41) can be extended by Thr, by Leu-Thr, or by Asp-Leu-Thr and/or can be acylated by an acyl group having 7 or less carbon atoms, e.g. acetyl, and such changes are considered to produce equivalent CRF antagonists. In addition, instead of the simple amide at the C-terminus, a lower alkyl-substituted amide, e.g. 1–4 carbon atoms, i.e. methylamide, ethylamide, etc., may be incorporated. As an alternative to a disulfide cyclizing bond, a carba or dicarba bond can be used (see U.S. Pat. No. 4,115,554) which is considered an equivalent. Such peptides are considered as being within the scope of the invention.

Various features of the invention are emphasized in the claims which follow.

What is claimed is:

1. A CRF peptide antagonist having the formula, or a nontoxic salt thereof:

(cyclo 30–33)D—Phe—His—Leu—Leu—Arg—Glu—Val—

—Leu—Glu—Nle—Ala—Arg—Ala—Glu—Gln—Leu—

—Ala—Gln—$R_{30}$—Ala—His—$R_{33}$—Asn—Arg—Lys—

-continued

—Leu—Nle—Glu—Ile—Ile—NH$_2$ wherein R$_{30}$ is Cys or Glu; R$_{33}$ is Cys, Lys or Orn; provided that when R$_{30}$ is Cys, R$_{33}$ is Cys and when R$_{30}$ is Glu, R$_{33}$ is Lys or Orn, and provided further that the N-terminus may be extended by Asp-Leu-Thr, Leu-Thr or Thr.

2. The CRF peptide antagonist of claim 1 having the formula:

(cyclo 30–33)H—D—Phe—His—Leu—Leu—Arg—Glu—Val—Leu—Glu—Nle—
Ala—Arg—Ala—Glu—Gln—Leu—Ala—Gln—Glu—Ala—His—Lys—Asn—Arg—
Lys—Leu—Nle—Glu—Ile—Ile—NH$_2$.

3. The CRF peptide antagonist of claim 1 having the formula:

(cyclo 30–33)H—D—Phe—His—Leu—Leu—Arg—Glu—Val—Leu—Glu—Nle—
Ala—Arg—Ala—Glu—Gln—Leu—Ala—Gln—Glu—Ala—His—Orn—Asn—Arg—
Lys—Leu—Nle—Glu—Ile—Ile—NH$_2$.

4. The CRF peptide antagonist of claim 1 having the formula:

(cyclo 30–33)H—D—Phe—His—Leu—Leu—Arg—Glu—Val—Leu—Glu—Nle—
Ala—Arg—Ala—Glu—Gln—Leu—Ala—Gln—Cys—Ala—His—Cys—Asn—Arg—
Lys—Leu—Nle—Glu—Ile—Ile—NH$_2$.

5. In a CRF peptide antagonist having the following formula, or a nontoxic salt thereof:

(cyclo 30-33)D-Phe-His-Leu-Leu-Arg-Glu-R$_{18}$-Leu-R$_{20}$-Nle-R$_{22}$-R$_{23}$-Ala-R$_{25}$-Gln-Leu-Ala-R$_{29}$-R$_{30}$-Ala-R$_{32}$-R$_{33}$-Asn-Arg-R$_{36}$-Leu-Nle-R$_{39}$-R$_{40}$-R$_{41}$-NH$_2$ wherein R$_{18}$ is Val, Nle or Met; R$_{20}$ is Glu or D-Glu; R$_{22}$ is Ala or Thr; R$_{23}$ is Arg or Lys; R$_{25}$ is Asp or Glu; R$_{29}$ is Gln or Glu; R$_{32}$ is His or Ala; R$_{36}$ is Lys or Leu; R$_{39}$ is Glu or Asp; R$_{40}$ is Ils or Glu; and R$_{41}$ is Ile or Ala; with R$_{20}$ being optionally be bonded to Lys$^{23}$, wherein the improvement comprises R$_{30}$ being either Glu or Cys and R$_{33}$ being Lys, Orn or Cys; provided, however, that when R$_{30}$ is Cys, R$_{33}$ is Cys; and when R$_{30}$ is Glu, R$_{33}$ is Orn or Lys.

6. The peptide of claim 5 wherein R$_{30}$ is Glu.

7. The peptide of claim 6 wherein R$_{33}$ is Lys.

8. The peptide of claim 5 wherein R$_{18}$ is Val, R$_{23}$ is Arg, R$_{32}$ is His, and R$_{40}$ is Ile.

9. The peptide of claim 8 wherein R$_{22}$ is Ala and R$_{25}$ is Glu.

10. A CRF peptide antagonist having the formula, or a nontoxic salt thereof:

(cyclo 30-33)R$_{12}$-His-Leu-Leu-Arg-Glu-Val-Leu-Glu-Nle-Ala-Arg-Ala-Glu-Gln-Leu-Ala-Gln-R$_{30}$-Ala-His-R$_{33}$-Asn-Arg-Lys-Leu-Nle-Glu-Ile-Ile-NH$_2$ wherein R$_{12}$ is D-Phe or D-Tyr, R$_{30}$ is Cys or Glu; R$_{33}$ is Cys, Lys or Orn; provided that when R$_{30}$ is Cys, R$_{33}$ is Cys and when R$_{30}$ is Glu, R$_{33}$ is Lys or Orn, and provided further that the N-terminus may be extended by Asp-Leu-Thr, Leu-Thr or Thr.

11. The peptide of claim 10 wherein R$_{33}$ is Lys.

12. In a CRF peptide antagonist having the following formula, or a nontoxic salt thereof:

(cyclo 30-33)Y-D-Phe-His-Leu-Leu-Arg-Glu-Val-R$_{19}$-R$_{20}$-R$_{21}$-Ala-R$_{23}$-Ala-R$_{25}$-Gln-R$_{27}$-Ala-Gln-R$_{30}$-Ala-His-R$_{33}$-Asn-Arg-Lys-Leu-Nle-R$_{39}$-Ile-R$_{41}$-NH$_2$ wherein Y is H, Ac, Fr, Acr, or Bz; R$_{19}$ is Leu or CML; R$_{20}$ is Glu or D-Glu; R$_{21}$ is Nle or Met; R$_{23}$ is Arg or Lys; R$_{25}$ is Asp or Glu; R$_{27}$ is Leu or CML; R$_{39}$ is Glu or Asp; R$_{41}$ is Ala or Ile; provided that the N-terminus may be extended by Asp-Leu-Thr, Leu-Thr or Thr, wherein the improvement comprises R$_{30}$ being either Glu or Cys and R$_{33}$ being Lys, Orn or Cys; provided, however, that when R$_{30}$ is Cys, R$_{33}$ is Cys; and when R$_{30}$ is Glu, R$_{33}$ is Orn or Lys.

13. The peptide of claim 12 wherein R$_{23}$ is Arg and R$_{25}$ is Glu.

14. The peptide of claim 12 wherein R$_{39}$ is Glu, and R$_{41}$ is Ile.

15. The peptide of claim 12 wherein R$_{27}$ is CML.

16. The peptide of claim 15 wherein R$_{19}$ is Leu.

\* \* \* \* \*